(12) United States Patent
Kuchenbecker et al.

(10) Patent No.: US 7,157,033 B2
(45) Date of Patent: Jan. 2, 2007

(54) METHOD AND APPARATUS FOR SCARFING FIBROUS SUBSTRATES

(75) Inventors: Dixon John Kuchenbecker, Neenah, WI (US); Bruce John Benson, Neenah, WI (US); Susan Joan Daniels, Neenah, WI (US); Michael Barth Venturino, Appleton, WI (US); Joseph Michael Kugler, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 194 days.

(21) Appl. No.: 10/954,821

(22) Filed: Sep. 29, 2004

(65) Prior Publication Data

US 2006/0071360 A1    Apr. 6, 2006

(51) Int. Cl.
*B27N 3/04* (2006.01)

(52) U.S. Cl. ............... 264/162; 264/518; 264/138; 425/80.1; 425/83.1; 425/289

(58) Field of Classification Search ............... None
See application file for complete search history.

(56) References Cited

U.S. PATENT DOCUMENTS

| | | | |
|---|---|---|---|
| 4,666,647 A | 5/1987 | Enloe et al. | |
| 4,761,258 A | 8/1988 | Enloe | |
| 4,927,582 A | 5/1990 | Bryson | |
| 5,466,409 A | 11/1995 | Partridge et al. | |
| 6,330,735 B1 | 12/2001 | Hahn et al. | |
| 6,416,697 B1 | 7/2002 | Venturino et al. | |
| 6,630,088 B1 | 10/2003 | Venturino et al. | |
| 2002/0153634 A1 | 10/2002 | Kugler et al. | |
| 2004/0098838 A1 | 5/2004 | Venturino et al. | |

*Primary Examiner*—Mary Lynn Theisen
(74) *Attorney, Agent, or Firm*—David J. Arteman (57) ABSTRACT

An apparatus for scarfing a fibrous web includes a rotatable scarfing roll with vacuum ports and an air moving source in fluid communication with the vacuum ports. The rotatable scarfing roll has a core member which includes a plurality of scarfing elements connected thereto and vacuum ports located therein. A method for scarfing a fibrous web includes providing a rotatable scarfing roll with vacuum ports and reducing scarfing wind by applying vacuum to the vacuum ports. A method for producing absorbent articles includes providing a fibrous web, contacting the fibrous web with a rotatable scarfing roll with vacuum ports to remove a portion of the fibrous web, applying vacuum to the vacuum ports to reduce scarfing wind, and producing an absorbent article with the fibrous web.

20 Claims, 8 Drawing Sheets

METHOD AND APPARATUS FOR SCARFING FIBROUS SUBSTRATES

BACKGROUND OF THE INVENTION

In the general practice of forming fibrous web materials, such as laid fibrous articles, it has been common to utilize a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous web. Typically the formed fibrous web has provided an interconnected plurality of appointed, fibrous pads. The fibrous web has been cut or otherwise segmented to provide individual pads. During the manufacturing operations, one or more scarfing operations have been employed to provide multiple functions. For example, the scarfing operation has been employed to level the peaks and valleys from the top of the formed fibrous web so that, from pad to pad along the length of the fibrous web, each pad can have substantially the same basis weight of absorbent material. Additionally, the scarfing operation has been employed to help control and regulate the desired basis weight distributions within each individual pad.

Adjustments to the basis weight distributions have, for example, been made by providing a foraminous forming surface that has predetermined depressions or pocket regions that allow an accumulation of relatively large amounts of absorbent material. Additionally, the location and configuration of the scarfing roll has been selectively adjusted. For example, by reducing the effective gap between the scarfing roll and the forming surface, the scarfing roll can be arranged to remove more material from the fibrous web. The amounts of removed material have been recirculated through the forming process, and have been employed to help fill the deeper pocket regions of the forming surface. The filling of the pocket regions has been accomplished by an over-forming of the pad with the selected absorbent material, and a mechanical redistribution of the absorbent material.

However, typical scarfing systems have provided a relatively course cut of absorbent material leading to higher variation in basis weight from pad to pad. As a result, there has been a continuing need for improved scarfing systems that can reliably produce and maintain a less variable basis weight distribution along the absorbent web.

SUMMARY OF THE INVENTION

The present invention provides a distinctive method and apparatus for scarfing a fibrous web. The apparatus for scarfing a fibrous web includes a rotatable scarfing roll with vacuum ports. The vacuum ports may be oblong or circular in shape. The apparatus may further include an air moving source in fluid communication with the vacuum ports. In some embodiments, a substantially airtight, non-contact, rotary union may form at least a portion of the fluid communication channel between the vacuum ports and the air moving source. The rotary union may include a labyrinth seal in some embodiments. The apparatus may also include a scarfing discharge fan. In some embodiments, the scarfing discharge fan may also be the air moving source.

The apparatus of the present invention may have a core member and a plurality of scarfing elements connected to the core member. The vacuum ports may be located in the core member. The scarfing elements include a distal end and a proximal end. The proximal end contacts the core member and the distal end is opposite the proximal end. In various embodiments, the distal end may be less than 4 inches from the vacuum ports, less than 2 inches from the vacuum ports, or less than 1 inch from the vacuum ports. The vacuum ports and the scarfing elements may be located in an alternating sequence radially around the rotatable scarfing roll.

One method for scarfing a fibrous web includes providing a rotatable scarfing roll with vacuum ports and reducing scarfing wind by applying vacuum to the vacuum ports. The method may include rotating the rotatable scarfing roll at least 1800 revolutions per minute.

One method for producing absorbent articles includes providing a fibrous web suitable for absorbent articles, contacting the fibrous web with a rotatable scarfing roll with vacuum ports to remove a portion of the fibrous web, applying vacuum to the vacuum ports to reduce scarfing wind; and producing an absorbent article with the fibrous web. The fibrous web may include cellulose fibers and superabsorbents. The fibrous web may include a scrim. The portion of the fibrous web removed may define a cut size less than 1 inch, less than 0.5 inch, or less than 0.25 inch. The rotatable scarfing roll may be rotating at least 1800 revolutions per minute or at least 2000 revolutions per minute.

BRIEF DESCRIPTION OF THE DRAWINGS

The invention will be more fully understood and further advantages will become apparent when reference is made to the following detailed description of the invention and to the drawings in which.

DETAILED DESCRIPTION OF THE DRAWINGS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

Figure 1:
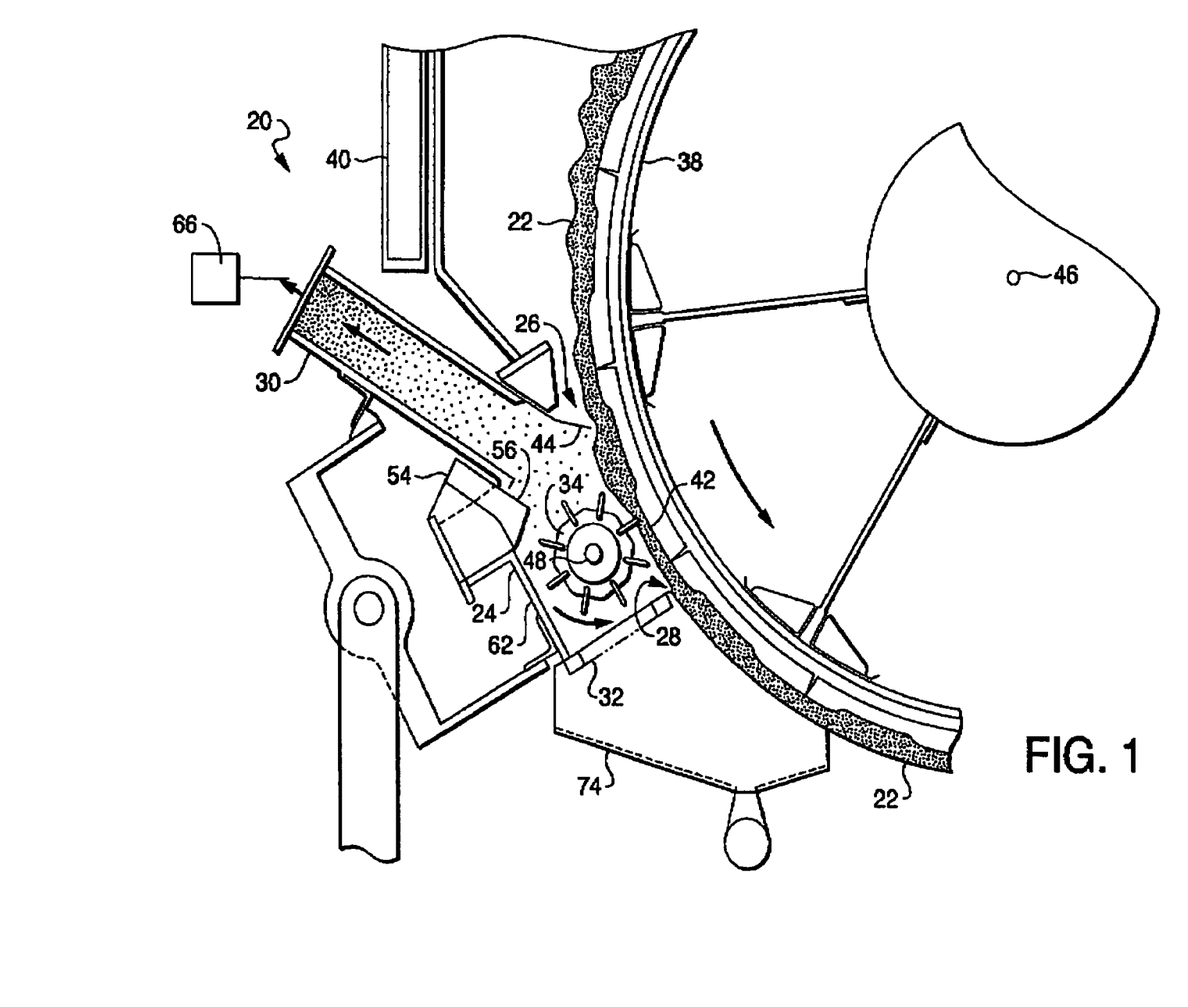
FIG. 1 shows a schematic, cross-sectional side view of a representative method and apparatus that incorporates the present invention.
Figure 2:
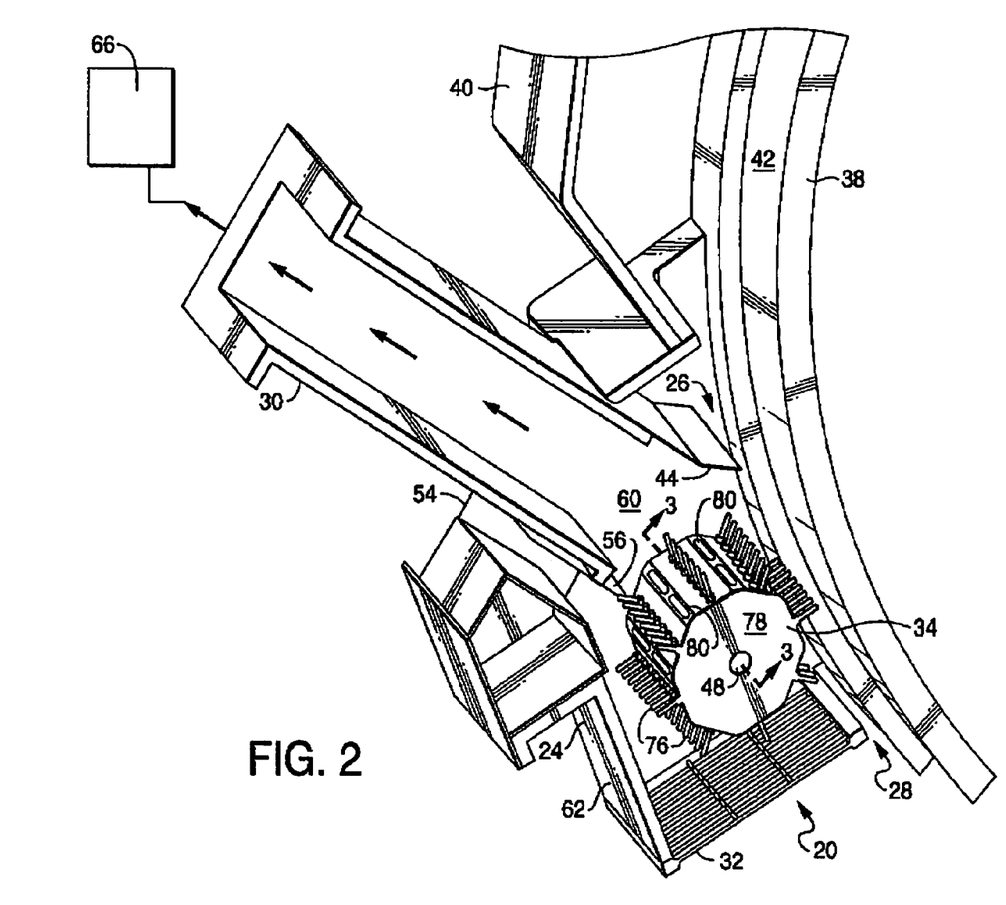
FIG. 2 shows a perspective view of a representative apparatus and method of the invention.

With reference to FIGS. 1 and 2, a distinctive method and apparatus 20 for scarfing a fibrous web 22 can include a scarfing housing 24 which has been provided with a web entrance portion 26, a web exit portion 28, a discharge conduit 30, and an air flow inlet 32. A rotatable scarfing roll 34 can be located in the scarfing housing 24. As used herein, the term "scarf", "scarfing" and variations thereof, relates to the action of mechanically removing of material from a substrate, such as a fibrous web. The mechanical removal can include contacting the substrate with one or more pins, fingers, flaps, ridges, projections, and the like, and combinations thereof to remove a select and controlled portion of the fibrous web.

As representatively shown, the method and apparatus 20 can include a forming chamber 40 and a transporter for moving a cooperating, foraminous forming surface 42 through the forming chamber. The fibrous web 22 is produced on the forming surface and the selected transporter can move the formed fibrous web out from the forming chamber 40 and into the scarfing housing 24. Additionally, the transporter can convey the fibrous web 22 through the scarfing housing 24 and out from the housing exit portion 28 for further processing. To provide desired air flows into and through the scarfing housing 24 and discharge conduit 30, a conventional air-moving system can be operatively connected to the discharge conduit 30. For example, a discharge fan 66 of suitable power and capacity can be connected to the discharge conduit 30. Such fans are well known in the art and are available from commercial vendors.

The method and apparatus of the present invention can be employed with any suitable fibrous web. The webs may be generated by various techniques, such as wet-forming techniques, foam forming techniques, airforming techniques or the like, as well as combinations thereof. Such webs may, for example, be air formed, and may contain natural and/or synthetic fibers, as well as superabsorbent material (SAM). The superabsorbent material can be in particulate form. In particular arrangements, the absorbent fiber can include cellulosic woodpulp fluff. The webs may additionally contain fibers or structures that reinforce, strengthen, or otherwise modify the fibrous web such as binder fibers, adhesive fibers, scrim, and the like, and combinations thereof. As used herein, the term "scrim" means a woven or a nonwoven material comprising elongate strands which are arranged so that the strands cross each other. More specifically, the strands may be arranged in a grid including parallel strands extending in the longitudinal (or "machine") direction MD and strands extending in the lateral (or "cross") direction CD defining rectangular openings or other shapes. Suitable scrim is described in greater detail in US 20040098838 A1, published May 27, 2004 to Venturino et al. In the illustrated arrangement, the transporter is provided by a rotatable forming drum 38. Alternatively, any other operative transporter mechanisms may be employed. For example, the transporter may be provided by an endless belt such as taught in U.S. Pat. No. 5,466,409 entitled FORMING BELT FOR THREE-DIMENSIONAL FORMING APPLICATIONS by Partridge et al. which issued Nov. 14, 1995, which is operatively driven by a conventional power system in a manner known in the art to move the fibrous web 22 from the forming chamber 40 and through the scarfing housing 24.

In the representatively shown configuration, the forming drum 38 has a drum axis of rotation 46, and the forming drum is configured to rotate in a counter-clockwise direction. Optionally, the forming drum 38 may be configured to rotate in a clockwise direction.

Suitable forming drum systems for producing airlaid fibrous webs are well known in the art. For example, see U.S. Pat. No. 4,666,647 entitled APPARATUS AND METHOD FOR FORMING A LAID FIBROUS WEB by K. Enloe et al. which issued May 19, 1987, U.S. Pat. No. 4,761,258 entitled CONTROLLED FORMATION OF LIGHT AND HEAVY FLUFF ZONES by K. Enloe which issued Aug. 2, 1988, U.S. Pat. No. 6,630,088 entitled FORMING MEDIA WITH ENHANCED AIR FLOW PROPERTIES by Venturino et al. which issued Oct. 7, 2003, and U.S. Pat. No. 6,330,735 entitled APPARATUS AND PROCESS FOR FORMING A LAID FIBROUS WEB WITH ENHANCED BASIS WEIGHT CAPABILITY by Hahn et al. which issued Dec. 18, 2001; the entire disclosures of which are incorporated herein by reference in a manner that is consistent herewith. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990 and U.S. Pat. No. 6,416,697 entitled METHOD FOR OBTAINING A DUAL STRATA DISTRIBUTION OF SUPERABSORBENT IN A FIBROUS MATRIX by Venturino et al. which issued Jul. 9, 2002; the entire disclosures of which are incorporated herein by reference in a manner that is consistent herewith.

The scarfing housing 24 is suitably constructed to provide a structure which can operatively enclose the fibrous web 22 during the scarfing operation. For example, the scarfing housing can include a wall member which provides the entrance portion 26, a wall member which provides the housing exit portion 28, housing side wall members 60 and a suitable housing cover wall member 62. The housing entrance portion 26 includes an entrance opening through which the fibrous web 22 enters the scarfing housing 24. The housing exit portion 28 includes an exit opening through which the fibrous web departs the scarfing housing 24 or further processing after the scarfing operation.

The scarfing roll 34 has an axis of rotation 48, and typically, the rotational axis 48 of the scarfing roll axis can be aligned substantially parallel to the rotational axis 46 of the forming drum. The scarfing roll axis and the drum axis may optionally be arranged to be non-parallel. Additionally, the scarfing roll can be positioned operatively adjacent the forming surface 42 provided by the forming drum 38, and the separation distance between the outer circumference of the scarfing roll 34 and the forming surface 42 can be selectively arranged to produce a desired thickness in the scarfed fibrous web. In the illustrated configuration, for example, the scarfing roll 34 can include a plurality of scarfing pins or other scarfing elements 76 that are operatively mounted and attached to a core member 78. The scarfing elements 76 have a proximal end 77 nearest the core member 78 and a distal end 75 opposite the proximal end 77 (see FIGS. 3 and 4).

The scarfing roll core can, for example, be generally cylindrical, and can have a diameter of about 3 to 16 inches (7.2 to 40.6 cm). In particular embodiments, the scarfing roll core can be about 5 inches (about 13 cm). Additionally, the outer diameter of the scarfing roll at the distal tips of the scarfing pins or other scarfing elements can be within the range of about 3 to 18 inches (about 7 to 45 cm). The scarfing roll can have an axial length that is within the range of about 1 to 20 inches (about 2.5 to 51 cm), and can include a selected pattern array of scarfing pins distributed along the outer surface of the scarfing roll core. For example, the scarfing elements may be arranged in rows that extend along the axial direction of the scarfing roll. In a particular arrangement the scarfing roll 34 can include approximately 8 rows of pins with approximately 0.5 inch (about 1.3 cm)

spacing between individual pins. The scarfing pins can have a diameter of about 0.125 to 0.50 inch (0.32 to 1.3 cm), and a length of about 0.5 to 4 inches (about 1.3 to 10 cm). Additionally, the rows of scarfing elements may be distributed around the circumference of the scarfing roll at substantially, equally spaced intervals. The scarfing elements can be integrated with the scarfing roll by any operative attachment system, such as a formation from a common material stock, screwing, welding or the like, as well as combinations thereof. For example, the scarfing elements may be threaded and screwed into the outer surface of the scarfing roll core. To help accommodate the mounting and attachment of the scarfing elements, flat areas may be formed on the surface of the scarfing roll.

The scarfing roll 34 is operatively rotated by a suitable drive mechanism, such as an electrical motor. Any other operative drive mechanism may alternatively be employed. In the representatively shown configuration, the scarfing roll 34 can be rotated at any operative speed that is sufficient to provide the desired scarfing operation. For example, the rotational speed of the scarfing roll can be within the range of about 900 to 7000 RPM (revolutions per minute), or more, to provide desired levels of performance. In a particular arrangement the rotational speed of the scarfing roll can be about 3000 RPM. In other embodiments, the rotational speed of the scarfing roll can be at least 1800 RPM and at least 2000 RPM.

In a desired arrangement, the scarfing roll 34 is operatively rotated in a direction such that when the scarfing pins contact the web, the scarfing pins are translated in a direction that is counter to the movement direction of the fibrous web 22. Alternatively, the scarfing roll 34 can be rotated such that when the pins are contacting the fibrous web, the scarfing pins are traveling in substantially the same direction as the movement direction of the fibrous web 22.

The scarfing roll 34 can rotate at a relatively high rate of speed to provide an operative scarfing motion. As representatively shown, the resulting scarfing motion can be in a direction that is substantially opposite to the movement direction of the formed fibrous web 22. This arrangement can generate an "explosive" impact when the scarfing pins (or other scarfing elements) contact the formed web 22. As the pins continue to move through the web material, most (but not necessarily all) of the scarfed and removed material can be projected forward along the movement direction of the scarfing pins. Generally stated, the forward movement of the scarfed material is caused by the momentum imparted to the scarfed material by the impulse applied by the moving scarfing pins.

As the scarfing roll pins impact the web, velocity and momentum are imparted to the fibers and particles of scarfed material pad. It is important to transport the scarfed material away from the web at a transport rate that is at least equal to the rate at which the scarfed material is being driven and separated from the web. In a particular aspect, the transport mechanism can include a housing airflow through the scarfing housing.

If the airflow speed through the scarfing housing 24 is too high, aerodynamic forces may lift the fibrous web 22 away from the transport surface (e.g., forming surface 42). This web-lifting effect can cause plugging or jamming within the scarfing housing, and can create excessive variations in the final basis weight of the scarfed fibrous web 22. The airflow in the scarfing housing 24 is impacted by the vacuum airflow applied to the fibrous web 22 on the forming drum 38, the vacuum airflow conveying scarfed fibers away from the fibrous web 22, the turbulence created by the rotation of the scarfing roll 34 and scarfing elements 76, and the localized wind pressure generated by the scarfing elements 76.

The discharge conduit 30 can have any operative configuration. For example, the cross-sectional shape of the discharge conduit may be circular, oval, rectangular, polygonal, or the like, as well as combinations thereof. In the illustrated arrangement, the discharge conduit is substantially straight. In alternative arrangements, the discharge conduit may optionally include a curved, bent or otherwise nonlinear configuration.

The selected transporter, such as provided by the rotatable forming drum 38 and its associated forming surface 42, can convey the fibrous web 22 through the scarfing housing 24 at a selected web transport speed. In a particular aspect, the web transport speed can be at least a minimum of about 2 meters per second (about 590 ft/min). The web transport speed can alternatively be at least about 5 m/sec (about 984 ft/min), and optionally, can be at least about 7 m/sec (about 1378 ft/min) to provide improved performance. In other aspects, the web transport speed can be up to a maximum of about 17 m/sec (about 3400 ft/min), or more. The web transport speed can alternatively be up to about 14 m/sec (about 2800 ft/min), and optionally, can be up to about 11 m/sec (about 2200 ft/min) to provide improved effectiveness. In a particular arrangement, the speed of the moving web 22 can be about 5.1 m/sec (about 1000 ft/min).

As previously discussed, the scarfing roll 34 can rotate at a relatively high rate of speed to provide an operative scarfing motion. A typical scarfing roll may turn at about 1750 RPM while a typical forming drum may turn about 1000 ft/min. When the scarfing pins 76 contact the fibrous web 22 on the forming drum 38 a portion of the fibrous web 22 is removed or "cut". One way of calculating the coarseness of the cut is by determining the scarfing length per pin hit. Generally, the greater the scarfing length per pin hit the coarser the cut. For example, a scarfing roll turning at 1750 RPM with 8 rows of pins against a forming drum turning at 1000 ft/min results in a scarfing length of 0.83 inches per pin hit. The scarfing length is calculated by determining that in one minute the scarfing roll rotates 1750 times and the forming drum travels 1000 feet. If there are 8 rows of pins around the circumference of the scarfing roll, then there are 14,000 pin hits in this minute (1750×8). Converting 1000 feet to inches and dividing by 14,000 yields a scarfing length of 0.857 inch per pin hit. This calculation can be represented as:

Scarfing Length (inches per pin hit)=forming drum speed (inches/minute)/(scarfing roll speed (RPM)*# pin hits/revolution)

Table 1 below illustrates several calculations showing that the scarfing length per pin hit decreases as the RPM and/or the number of pins per revolution increases. It is believed that the smaller the scarfing length per pin hit the finer the cut, the smoother the surface of the fibrous web, and the less variable the basis weight of the fibrous web. In other words, the scarfing roll is taking a greater number of "bites" in a given period of time but each bite is smaller, which minimizes the likelihood of large chunks being removed and thus improves weight variability. Also, smaller bites results in finer recycled fibers and less bundling, clumping, etc. As such, when the recycled fiber is reintroduced into the forming chamber there are fewer and smaller clumps forming part of the fibrous web, again reducing weight variability. This effect can be analogized to cutting a board with a saw blade having many teeth. Each tooth takes a small bite and creates fine saw dust and leaves the board smooth. In contrast a saw blade running at the same RPM but with fewer teeth takes larger bites per tooth, creates coarser saw dust (or chunks), and leaves the board rough and ragged.

TABLE 1

| Scarfing Roll (revolutions per minute) | Number of pins (rows per revolution) | Forming Drum (feet per minute) | Scarfing length (inches per pin hit) |
|---|---|---|---|
| 1750 | 8 | 1000 | 0.857 |
| 1750 | 10 | 1000 | 0.686 |
| 1750 | 12 | 1000 | 0.571 |
| 1750 | 14 | 1000 | 0.490 |
| 1900 | 8 | 1000 | 0.789 |
| 2000 | 8 | 1000 | 0.75 |
| 2100 | 8 | 1000 | 0.714 |
| 2200 | 8 | 1000 | 0.681 |
| 2400 | 12 | 1000 | 0.417 |
| 3600 | 12 | 1000 | 0.278 |

Previous efforts to reduce the scarfing length (i.e., cut coarseness) have involved increasing the RPM of the scarfing roll, adding more rows of pins, or combinations of both, Surprisingly, these changes did not improve basis weight variability, but instead resulted in degradation of the process variability. The degradation is believed to be a result of excessive wind pressure generated by the rotating pins. Adding additional pins or increasing the scarfing roll revolutions per minute increases the wind pressure and exacerbates the basis weight problem because the wind pressure can blow the fibers off the drum prior to the pins contacting the pad.

This invention overcomes the scarfing wind problem by porting the scarfing roll and applying a vacuum. The vacuum reduces or eliminates the wind pressure at or near the source by permitting the flow of external positive air pressure through the vacuum ports and into the negative pressurized vacuum chamber. By regulating the vacuum level within the scarfing roll, one can overcome and remove the positive air pressure caused by the rotating pins. The vacuum level is increased until fibers start to enter the scarfing roll. The vacuum level is then reduced slightly to reach a level of maximum scarfing wind reduction without conveying fibers. Once the scarfing wind pressure is reduced or eliminated, the fibers remain on the drum allowing a finer cut, smoother finish, and lower weight variability. Traditionally, higher vacuum was required in the forming drum to help hold down the fibers, but because the fibers tend to remain on the drum when utilizing the present invention, the vacuum required within the forming drum can be reduced providing a cost savings. Additionally, the reduced vacuum allows for a reduced density pad which in turn allows for a more accurate machining by the scarfing elements and a less variable basis weight.

In the event that fibers would enter the internal portions of the scarfing roll, it would be desirable for the vacuum source to be the scarfing return fan. This not only eliminates the need of procuring additional hardware, but it would also recycle any fugitive fibers back into the forming system.

Figure 3:
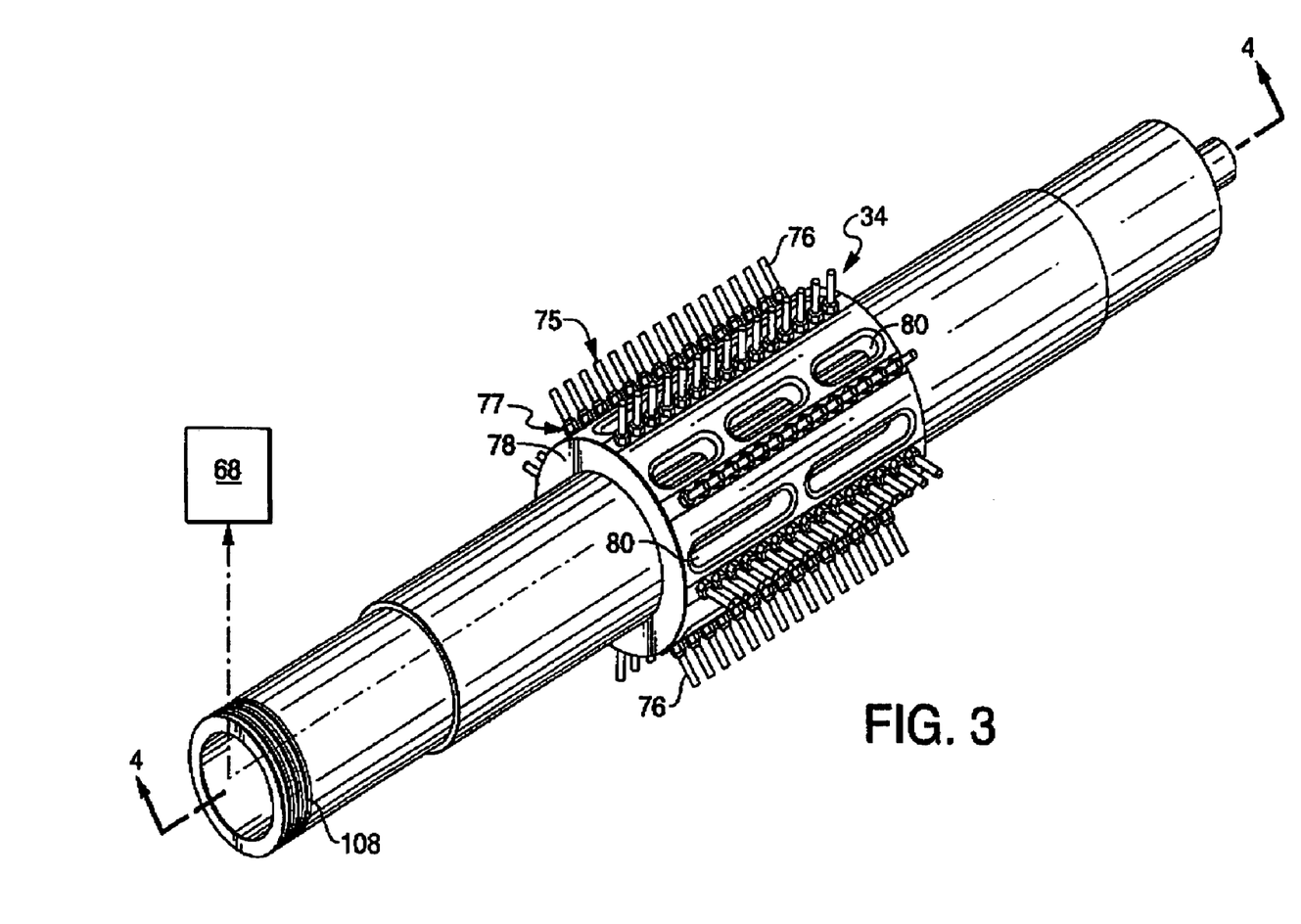
FIG. 3 shows a perspective view of a representative apparatus of the invention.
Figure 4:
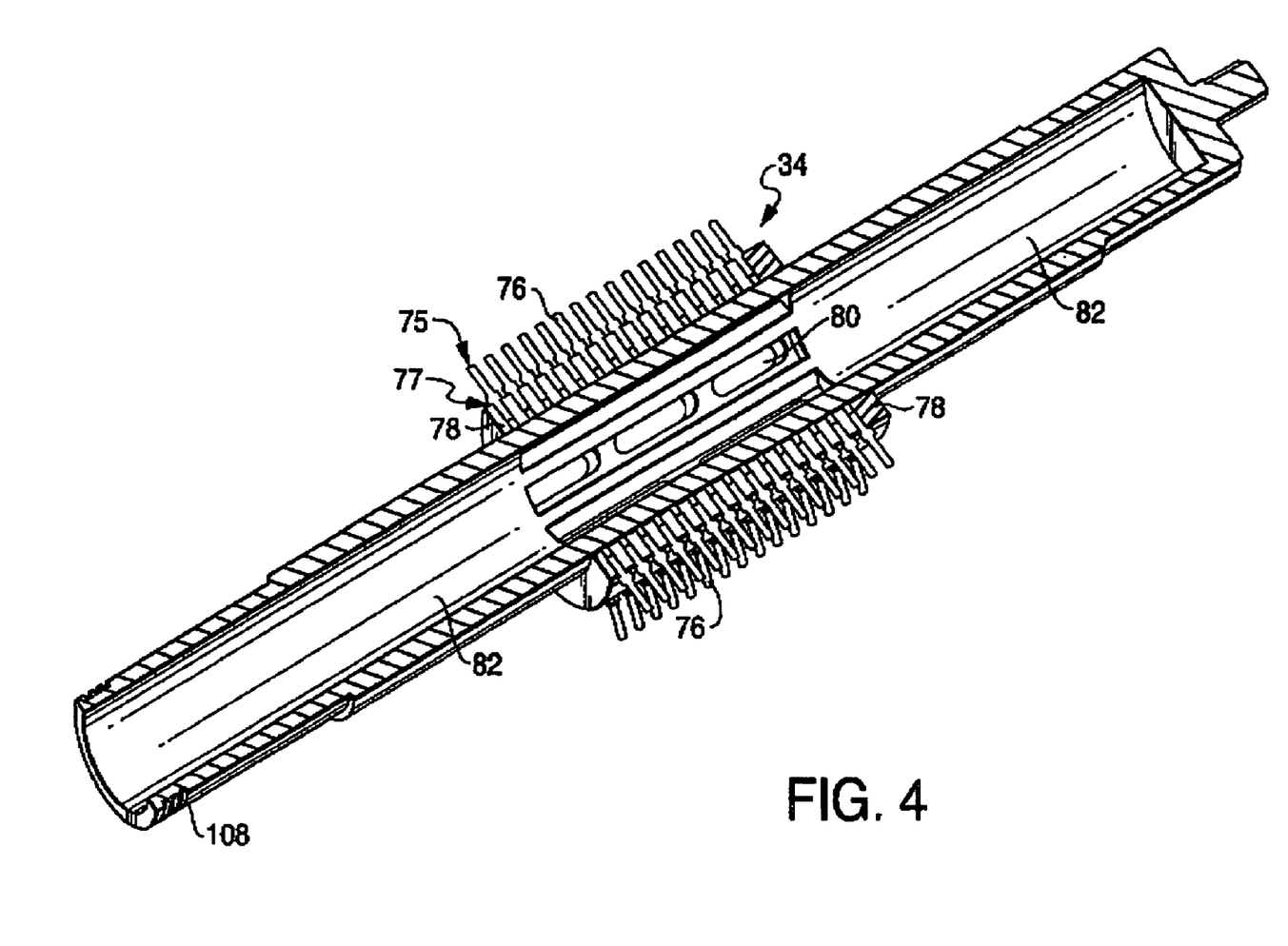
FIG. 4 shows a perspective, cross-sectional view of the scarfing roll of FIG. 3 taken along the line 4—4.

Referring now to FIGS. 2, 3, and 4 the scarfing roll 34 has a plurality of vacuum ports 80 that are in fluid communication with a vacuum chamber 82 within the core member 78. To provide desired air flows into and through the scarfing roll 34, a conventional air-moving system can be operatively connected to vacuum chamber 82. For example, a discharge fan 68 of suitable power and capacity can be connected to the vacuum chamber 82. In some embodiments, the scarfing discharge fan 66 may be used to supply the vacuum to the vacuum chamber 82. The advantages of using the same fan include reduction in necessary equipment and recovery of fugitive fibers and super absorbent that may enter the vacuum chamber 82. Such fans are well known in the art and are available from commercial vendors. Alternatively or in addition, other devices for moving air can be utilized, for example, air pumps, blowers or the like, as well as combinations thereof.

Figure 5:
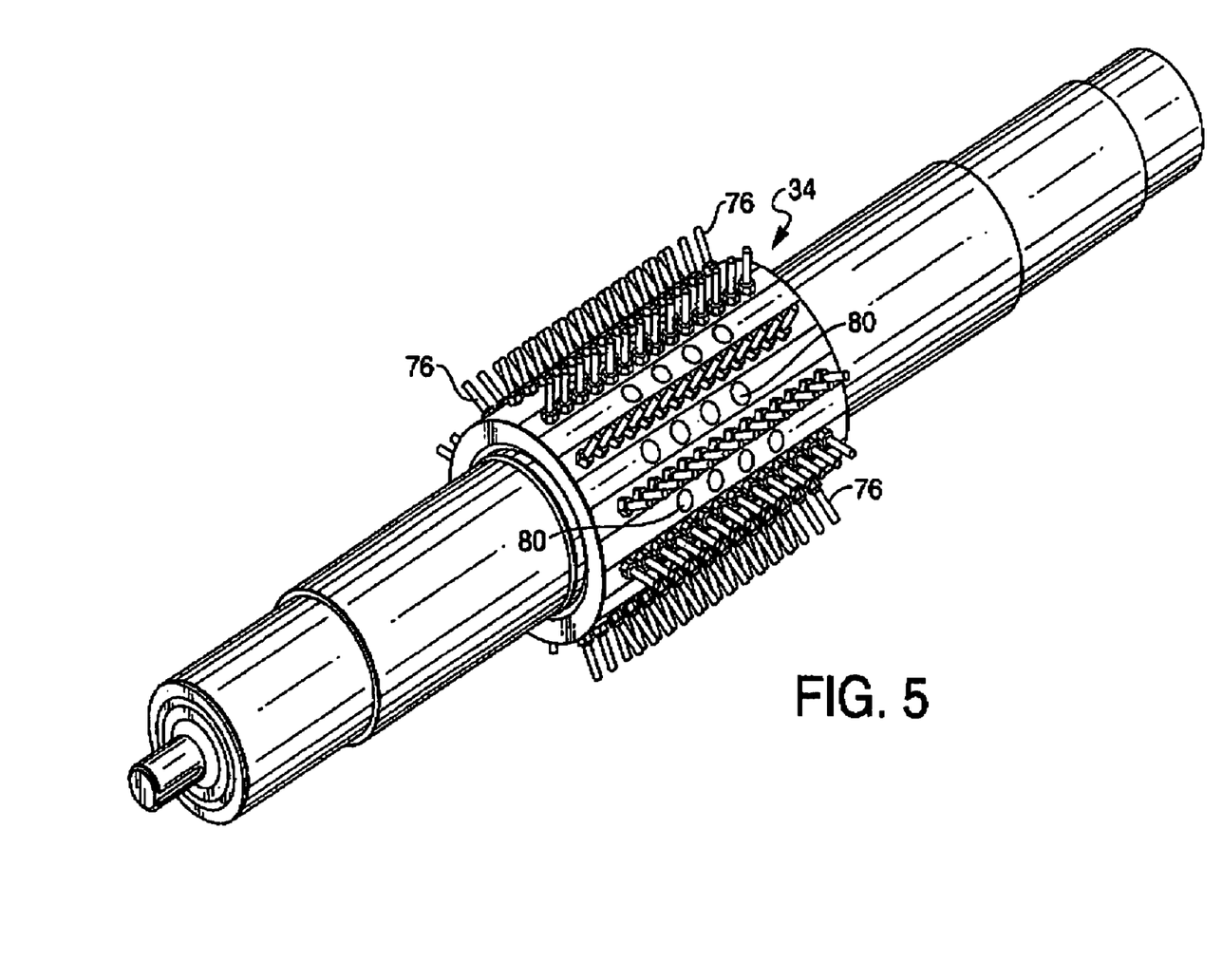
FIG. 5 shows a perspective view of a representative apparatus of the invention.

The vacuum ports 80 may be provided in any operative shape. For example, the cross-sectional shape of the vacuum ports 80 may be elongated oval as illustrated in FIG. 3, circular as illustrated in FIG. 5, oval, rectangular, polygonal, or the like, as well as combinations thereof. The vacuum ports 80 may have chamfered edges, beveled edges, radius edges, bell-shaped edges, or other suitable shapes, or combinations thereof. The addition of chamfers or other shapes to the edges of the vacuum ports 80 creates better air flow into the vacuum ports 80 and reduces the air drag.

The vacuum ports 80 in the present embodiments are illustrated in the core member 78 but could alternatively be located in the scarfing elements 76 or exterior to the scarfing roll 34 so long as the vacuum ports 80 are sufficiently close to the scarfing elements 76 to reduce or eliminate the wind pressure generated by the rotating scarfing elements 76 yet not induce fiber flow into the vacuum ports 80. In some embodiments, the distal end 75 of scarfing elements 76 are less than 4 inches (10.2 cm) from the vacuum ports 80. In other embodiments, the distal ends 75 are less than 3 inches (7.6 cm), less than 2 inches.(5.1 cm), or less than 1 inch (2.5 cm) from the vacuum ports 80.

Figure 6:
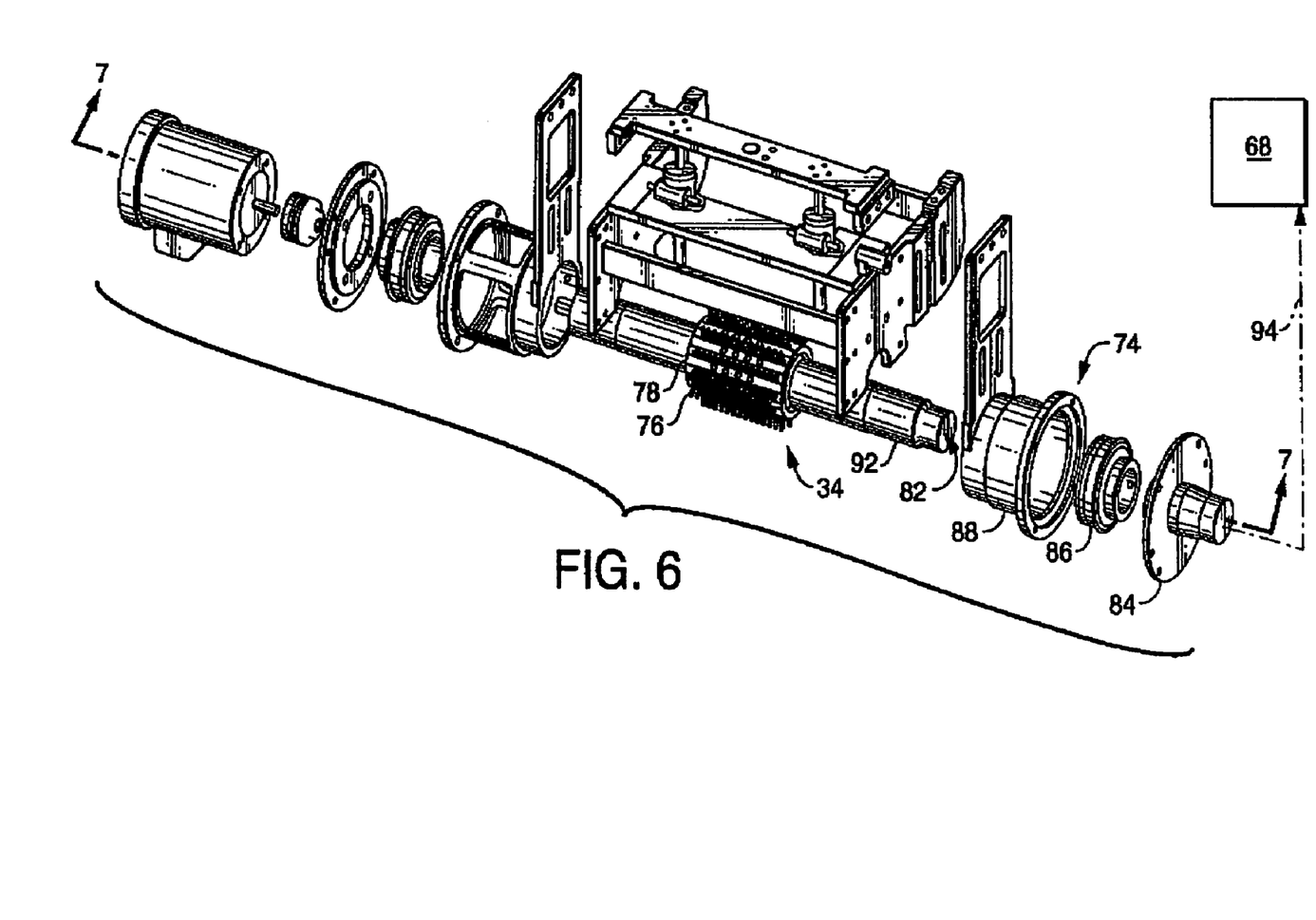
FIG. 6 shows a perspective view of a representative apparatus of the invention with the components exploded for illustration.
Figure 7:
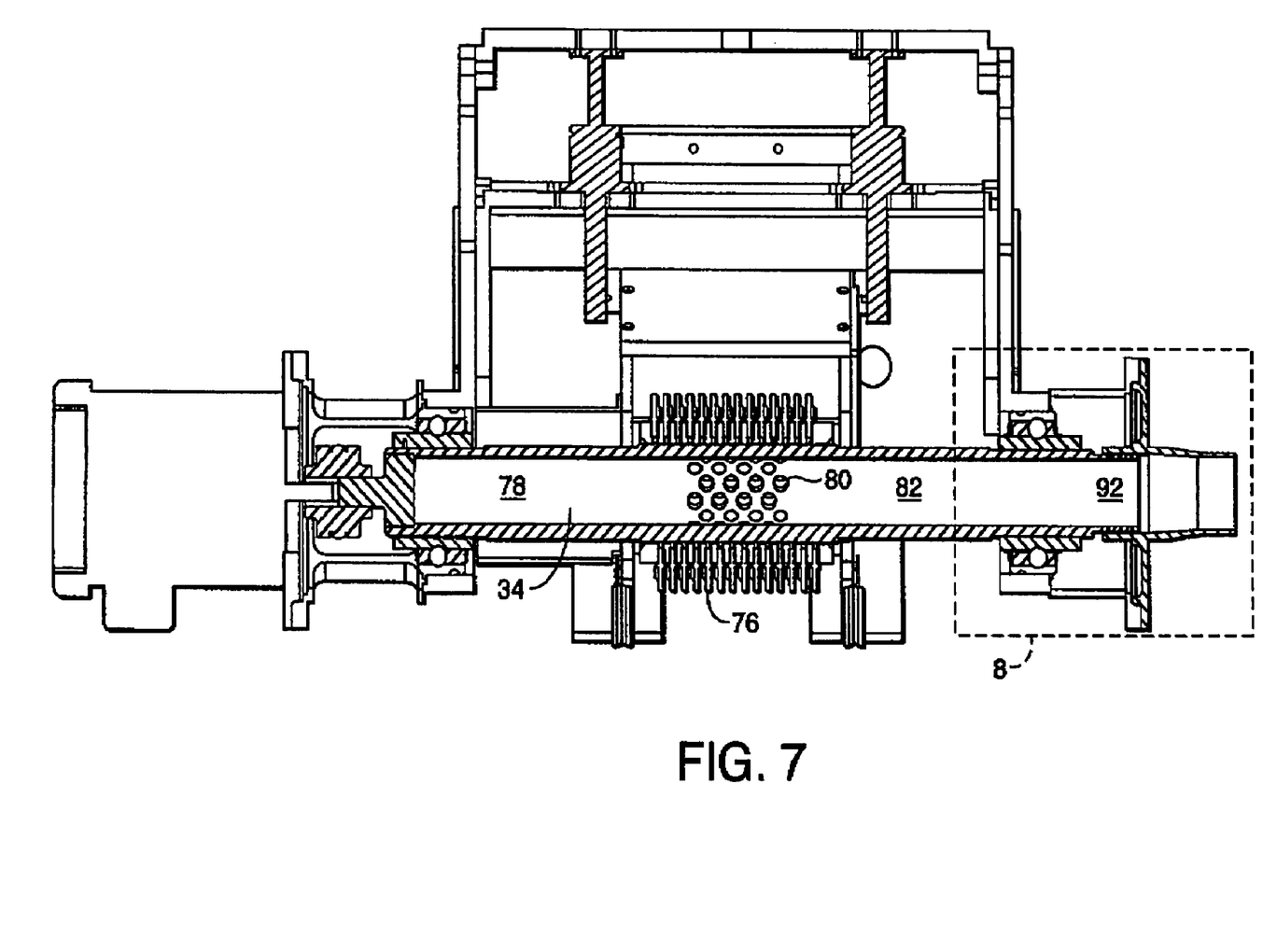
FIG. 7 shows a cross-sectional view of the apparatus of FIG. 6 taken along line 7—7 with the components assembled.
Figure 8:
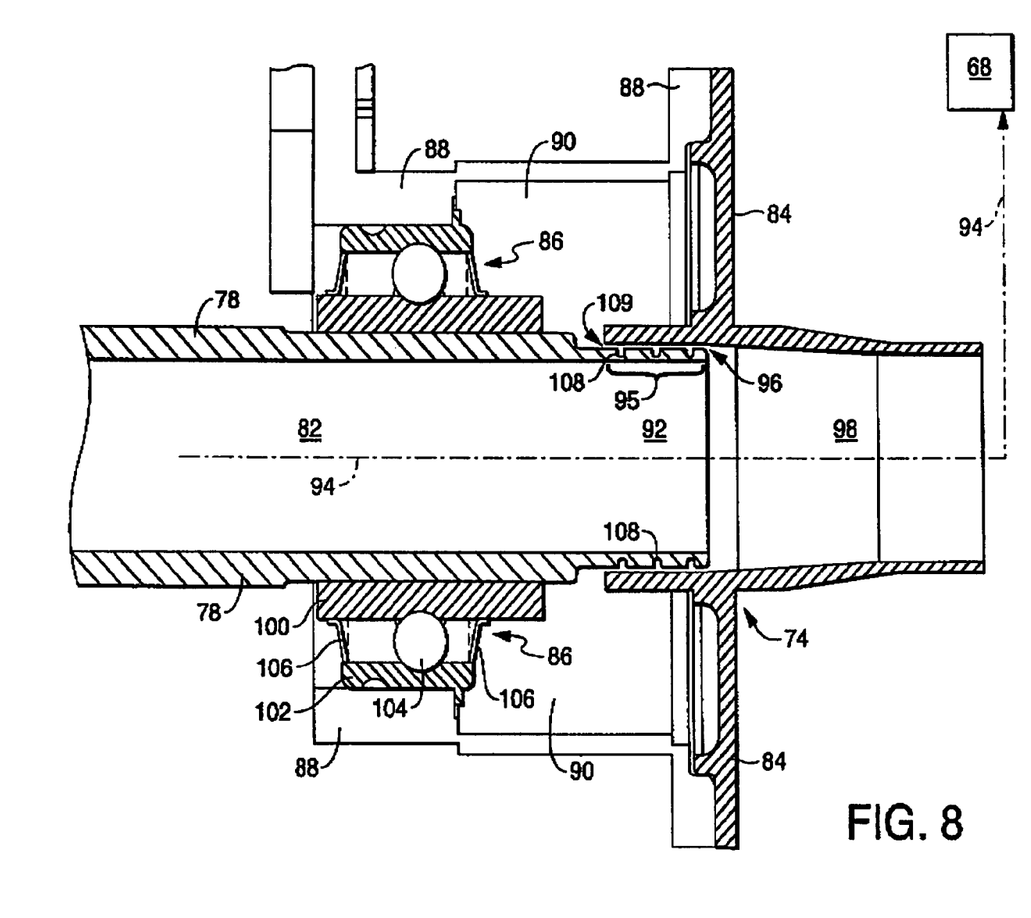
FIG. 8 shows an enlarged cross-sectional view of the portion of the apparatus of FIG. 7 contained within Box 8.

Referring to FIGS. 6, 7, and 8, an exemplary apparatus is illustrated. FIG. 6 is an exploded perspective view of one embodiment of the apparatus of the present invention. FIG. 6 illustrates the relative positions of the rotatable scarfing roll 34, the vacuum chamber 82, a vacuum chamber extension 92, and a rotary union 74. The rotary union 74 includes an outer housing 88, a bearing assembly 86, and a fixed flange 84. FIG. 7 is a cross-sectional perspective view of the assembled apparatus of FIG. 6 taken along line 7—7.

FIG. 8 illustrates an enlarged view of the boxed portion 8 of the apparatus of FIG. 7. The apparatus of FIG. 8 illustrates the non-contact rotary union generally indicated at 74 that may be used in some embodiments of the present invention to operatively join, in fluid communication, the vacuum chamber 82 to an air source. In these embodiments, a discharge fan 68 is operatively connected to the fixed flange 84 to move air generally in the direction indicated by dashed line 94 through a flange passage 98. The vacuum chamber extension 92 engages the bearing assembly 86 and partially penetrates the fixed flange 84 creating an overlap region 95 and a gap 96. The bearing assembly 86 is positioned in the outer housing 88 and the bearing assembly 86 holds the vacuum chamber extension 92 such that there is little to no contact with the fixed flange 84 in the overlap region 95 when the vacuum chamber extension 92 rotates during operation. The fixed flange 84 is operably affixed, either directly or through an intermediate structure, to the outer housing 88. The bearing assembly 86, the outer housing 88, and the fixed flange 84 define a vacuum sealing chamber 90. The vacuum sealing chamber 90 is in fluid communication with the flange passage 98 via the gap 96. However, there is minimal vacuum leakage through the gap 96 in the overlap region 95 because the vacuum sealing chamber 90 is sealed by the bearing assembly 86, the outer housing 88, and the fixed flange 84. This configuration of the rotary union 74 provides a non-contact, non-wearing, non-friction junction that maintains a vacuum seal while allowing the shaft to rotate freely. The advantage of this arrangement is that vacuum can be applied to the vacuum chamber 82, via the flange passage 98, and the vacuum chamber extension 92 while the vacuum chamber 82 continues to rotate with the scarfing roll 34.

In various embodiments, the bearing assembly 86 can include an inner race 100, an outer race 102, a rolling element 104, and seals 106. Such assemblies are known to those skilled in the art. For example, suitable bearing assemblies include SEALMASTER ER-52 bearings from Emerson Power Transmission, a division of Emerson Electric, located in St. Louis Mo.

In various embodiments, the vacuum chamber extension 92 may include one or more grooves 108 around the outer circumference of the core member 78 as illustrated in FIGS. 3, 4, and 8. When the vacuum chamber extension 92 is inserted into the fixed flange 84, the grooves 108, in combination with the gap 96, form a labyrinth seal 109. A labyrinth seal 109 inhibits air flow by creating air passages with variable available volume. The air passing through the labyrinth seal 109 encounters a relatively small available volume when there is only the gap 96 but encounters a larger available volume when passing a groove 109. This change in relative volume creates turbulent airflow and inhibits the passage of air. In alternative embodiments, the inner surface of the fixed flange 84 may contain grooves in the overlap region 95 creating an alternative labyrinth seal. In yet other embodiments, both the vacuum chamber extension 92 and the fixed flange 84 may include grooves to create a labyrinth seal.

Other function rolls, such as cutting rolls, perforating rolls, embossing rolls, etc., may benefit from vacuum porting as taught herein. However, it is believed that the benefits of the present invention are most evident with scarfing rolls because the relative wind pressure is greater than with other function rolls because the projections are generally longer on scarfing rolls versus other function rolls. Likewise, other webs, such as stable films, nonwovens, and the like, may benefit from the vacuum porting taught herein by reducing wrinkles and improving tracking. However, greater benefits in wind reduction are likely to be observed when using lower density fibrous sheets that are more susceptible to the effects of wind.

Various attachments and securements may be employed in the constructions of the method and apparatus of the invention, it should be readily apparent that any conventional attachment or securement technique may be employed. Such techniques may, for example, include adhesives, welds, screws, bolts, nuts, rivets, pins, latches, clamps or the like, as well as combinations thereof.

Similarly, it should be readily apparent that any conventional material may be employed to construct the various components incorporated into the method and apparatus of the invention. Such materials can include synthetic polymers, fiberglass-resin composites, carbon fiber-resin composites, metallic composites, ceramic composites, and the like, as well as combinations thereof. The materials are typically selected to provide desired levels of strength, durability, ease of manufacture, and ease of maintenance.

While the invention has been described in detail with respect to specific embodiments thereof, it will be appreciated that those skilled in the art, upon attaining an understanding of the foregoing will readily conceive of alterations to, variations of and equivalents to these embodiments. Accordingly, the scope of the present invention should be assessed as that of the appended claims and any equivalents thereto.

The invention claimed is:

1. An apparatus for scarfing a fibrous web comprising, a rotatable scarfing roll with vacuum ports.

2. The apparatus of claim 1 wherein the vacuum ports are oblong or circular in shape.

3. The apparatus of claim 1 further comprising an air moving source in fluid communication with the vacuum ports, wherein a substantially airtight, non-contact, rotary union forms at least a portion of a fluid communication channel between the vacuum ports and the air moving source.

4. The apparatus of claim 3 further comprising a scarfing discharge fan, wherein the scarfing discharge fan is also the air moving source.

5. The apparatus of claim 3 wherein the rotary union includes a labyrinth seal.

6. The apparatus of claim 1 wherein the rotatable scarfing roll has a core member and a plurality of scarfing elements connected to the core member.

7. The apparatus of claim 6 wherein the vacuum ports are located in the core member, the scarfing elements include a distal end and a proximal end, the proximal end contacts the core member and the distal end is less than 4 inches from the vacuum ports.

8. The apparatus of claim 6 wherein the vacuum ports are located in the core member, the scarfing elements include a distal end and a proximal end, the proximal end contacts the core member and the distal end is less than 2 inches from the vacuum ports.

9. The apparatus of claim 6 wherein the vacuum ports are located in the core member, the scarfing elements include a distal end and a proximal end, the proximal end contacts the core member and the distal end is less than 1 inch from the vacuum ports.

10. The apparatus of claim 6 wherein the vacuum ports are located in the core member and the vacuum ports and the scarfing elements are located in an alternating sequence radially around the rotatable scarfing roll.

11. A method for scarfing a fibrous web comprising,
   a. providing a rotatable scarfing roll with vacuum ports; and
   b. reducing scarfing wind by applying vacuum to the vacuum ports.

12. The method of claim 11 further comprising, rotating the rotatable scarfing roll at least 1800 revolutions per minute.

13. A method for producing absorbent articles comprising,
   a. providing a fibrous web suitable for absorbent articles;
   b. contacting the fibrous web with a rotatable scarfing roll with vacuum ports to remove a portion of the fibrous web;
   c. applying vacuum to the vacuum ports to reduce scarfing wind; and
   d. producing an absorbent article with the fibrous web.

14. The method of claim 13 wherein the fibrous web comprises cellulose fibers and superabsorbents.

15. The method of claim 13 wherein the fibrous web comprises a scrim.

16. The method of claim 13 wherein the portion of the fibrous web removed defines a cut size less than 1 inch.

17. The method of claim 13 wherein the portion of the fibrous web removed defines a cut size less than 0.5 inch.

18. The method of claim 13 wherein the portion of the fibrous web removed defines a cut size less than 0.25 inch.

19. The method of claim 13 wherein the rotatable scarfing roll is rotating at least 1800 revolutions per minute.

20. The method of claim 13 further comprising, rotating the rotatable scarfing roll at least 2000 revolutions per minute.

* * * * *